(12) United States Patent
Tian et al.

(10) Patent No.: US 12,343,321 B1
(45) Date of Patent: Jul. 1, 2025

(54) METHOD FOR AMELIORATING OR AVOIDING THE ADVERSE EFFECTS OF EXOGENOUS GONADOTROPINS ON REPRODUCTIVE PERFORMANCE

(71) Applicant: CHINA AGRICULTURAL UNIVERSITY, Beijing (CN)

(72) Inventors: Jianhui Tian, Beijing (CN); Shumin Wang, Beijing (CN); Lei An, Beijing (CN); Yue Wang, Beijing (CN); Yusheng Qin, Beijing (CN); Wei Zhao, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 18/899,511

(22) Filed: Sep. 27, 2024

(30) Foreign Application Priority Data

May 10, 2024 (CN) .......................... 202410578838.2

(51) Int. Cl.

| | | |
|---|---|---|
| *A61K 31/197* | (2006.01) | |
| *A61K 9/00* | (2006.01) | |
| *A61K 31/07* | (2006.01) | |
| *A61K 31/575* | (2006.01) | |
| *A61K 38/09* | (2006.01) | |
| *A61K 45/06* | (2006.01) | |

(52) U.S. Cl.
CPC .......... *A61K 31/197* (2013.01); *A61K 9/0056* (2013.01); *A61K 31/07* (2013.01); *A61K 31/575* (2013.01); *A61K 38/09* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2002/0028849 | A1* | 3/2002 | Godkin | A61K 31/07 800/21 |
| 2008/0200548 | A1* | 8/2008 | Goldstein | A61P 15/00 600/35 |

OTHER PUBLICATIONS

The translation of Tian et al., CN 110063812, published Jul. 30, 2019 (Year: 2019).*
Zięcik et al., Journal of Animal and Feed Sciences, 9, 2000, 471-478 (Year: 2000).*
Wähner et al., Reprod Dom Anim. 31, 477-482 (1996) (Year: 1996).*
First Office Action issued in Chinese Patent Application No. 202410578838.2; mailed Jun. 8, 2024; 11 pgs.
Fu, Kaibin; "Study on the regulatory mechanism of N-acetylcysteine on uterine receptivity in early pregnancy of goats"; Chinese Master's Thesis Full-text Database Agriculture Science and Technology, Apr. 15, 2024, 14 pgs.
Liu, Guang-mang, et al.; "Effects of the Iron and Vitamin A Levels on Uteriue Protein Secretion and Embryo Survival Rate in Mice"; Chinse Journal of Animal Nutrition; vol. 9, No. 4, pp. 392-400, Dec. 31, 2007.

* cited by examiner

*Primary Examiner* — Christina M Borgeest
(74) *Attorney, Agent, or Firm* — HAUPTMAN HAM, LLP

(57) ABSTRACT

The disclosure relates to the field of biology and provides a breeding method for ameliorating or avoiding the adverse effects of exogenous gonadotropins on reproductive performance, which comprises administrating N-acetylcysteine and vitamin A prior to the exogenous gonadotropin treatment. The disclosure can effectively improve the reproductive performance, including improving the uterine receptivity and pregnancy outcome after exogenous gonadotropins treatment, such as embryo implantation rate, the status of embryo development after implantation, pregnancy rate, live birth, health condition of born offspring, and other effects, by using a combination of N-acetylcysteine and vitamin A. Moreover, the combination of N-acetylcysteine and vitamin A has synergistic effect and has a wide application prospect, for example, in animal husbandry to realize the reproduction regulation and control management of animals including domestic animals such as pigs, horses, cattle, and the like and realize batch production, as well as in the field of assisted reproduction, with high application value.

6 Claims, 4 Drawing Sheets

METHOD FOR AMELIORATING OR AVOIDING THE ADVERSE EFFECTS OF EXOGENOUS GONADOTROPINS ON REPRODUCTIVE PERFORMANCE

RELATED APPLICATIONS

The present application claims priority from Chinese Application Number 202410578838.2 filed on May 10, 2024, the disclosure of which is hereby incorporated by reference herein in its entirety.

TECHNICAL FIELD

The disclosure relates to the field of biology. In particular, the disclosure relates to a method for ameliorating or avoiding the effect of exogenous gonadotropins on reproductive performance of female animals.

BACKGROUND

Gonadotropins are glycoprotein hormones that regulate the development of mammalian gonads and gametes, and promote the production and secretion of sex hormones. During human assisted reproduction applications, exogenous follicle-stimulating hormone (FSH) and human chorionic gonadotropin (hCG, used in place of luteinizing hormone LH to stimulate ovulation) are commonly used to induce superovulation in patients for collecting more eggs. In the domestic animals industry, for cost and half-life considerations, equine chorionic gonadotropin (eCG) and gonadotropin-releasing hormone analogues (GnRH analogues, used to induce endogenous LH release) are generally selected to induce follicular development and ovulation of animals, used for intensive management system.

Gonadotropin is an effective means for inducing follicular development and ovulation in human assisted reproduction and animals reproduction management. The ovulation rate can be increased, and the ovulation time can also be controlled more accurately, which facilitates large-scale reproduction management. However, the use of exogenous gonadotropins has long been faced with problems of reduced pregnancy rate, embryo loss, delayed fetal development after implantation, and even abortion. For example, eCG/hCG superovulation treatment causes problems of limited fetal growth and development and increased fetal absorption rate after mouse implantation, increased embryo loss rate of pregnant sows, decreased clinical pregnancy rate of assisted reproduction, and the like. In view of the above problems, the prior art has certain improvements. For example, the prior art suggests that N-acetylcysteine can improve pregnancy rate for in vitro fertilization-embryo transfer by alleviating uterine contractile activity; in addition, N-acetylcysteine may enable targeted improvements of the uterine environment, improve the development capability of early embryos, increase the number of implanted embryos, improve litter birth, or improve the reproductive performance of female animals after the application of the timed insemination technology, and effectively improve the pregnancy rate of sows, and the like. In addition, in the assisted reproduction field, in order to ameliorate or avoid the adverse effects of exogenous gonadotropins on uterine receptivity and pregnancy outcome, a frozen embryo transfer has been adopted, i.e., after a female receives exogenous gonadotropin treatment and ovum pick-up, and fresh embryo transfer is not carried out and frozen whole embryos are selected.in order to improve the pregnancy rate. However, the cryopreservation of embryos has a significant impact on subsequent embryonic development and the offspring health. For this, a method capable of ameliorating or avoiding the adverse effects of exogenous gonadotropins on the uterine receptivity and the pregnancy outcome is needed urgently in the assisted reproduction field.

However, since the molecular mechanism for adverse effects by gonadotropins has been elusive, effective measures to ameliorate these side-effects and improve endometrial receptivity and pregnancy outcome after with exogenous gonadotropins treatment.

SUMMARY

The disclosure aims to resolve, at least in part, the technical problems existing in the prior art. For this, the disclosure on one aspect provides a method for ameliorating or avoiding the adverse effects of exogenous gonadotropins on reproductive performance of female animals, and on another aspect provides a method for improving reproductive performance of a subject treated with exogenous gonadotropins comprising administrating the subject with a combination of N-acetylcysteine and vitamin A, and on third aspect provides a method for inhibiting ERα-FGF-pERK-cell cycle signaling pathway in a cell comprising administrating a combination of N-acetylcysteine and the vitamin A to the cell. The disclosure can effectively ameliorate or avoid the reproductive performance after exogenous gonadotropins treatment, including the uterine receptivity and pregnancy outcome, such as embryo implantation rate, the status of embryo development after implantation, pregnancy rate, live birth, offspring health, and the like, by co-administration of N-acetylcysteine and vitamin A. Moreover, the combination of N-acetylcysteine and vitamin A has a synergistic effect and a wide application perspective. For example, in animal husbandry to realize the reproduction management and batch production in domestic animals such as swine, horses, cattle, and the like, and can also be used in the field of assisted reproduction.

To be clear, the disclosure has been completed based on the following inventories:

The inventors found that uterine receptivity was damaged after exogenous gonadotropins stimulation to induce superovulation, which is a major cause of the reduction of pregnancy rate and embryo loss. The findings demonstrate that the exogenous gonadotropin treatment can lead to over-activation of ERα-FGF-pERK-cell cycle signaling pathway (FIGS. 1A-1C) of endometrium, and further study showed that abnormally increased estrogen receptor (ERα) protein levels were observed in the endometrial epithelial cells during the establishment of uterine receptivity, and ERα cause abnormal increase of the fibroblast growth factor (FGF) family members protein levels in the endometrial stroma. The elevated FGF causes the hyperphosphorylation and hyperactivation of FGFR-ERK pathway of endometrial epithelial cells via the paracrine actions. And then the persistent overproliferation of the endometrial epithelial cells impact the establishment of the uterine receptivity and the development both before and after birth.

In view of this, since dysregulation of ERα-FGF-pERK-cell cycle signaling leads to uterine receptivity decrease after exogenous gonadotropin treatment, drug screenings were selected against different targets. Specifically, multiple treatments have been attempted against one or more different targets, but the desired effects can't be achieved by any inhibition maneuver. For example, BGJ398, an inhibitor for FGF receptors could significantly increase the number of implantation sites in the early pregnancy, but negatively affect fetal development, leading abnormal development of the fetus after implantation.

Vitamin A (also referred to herein as "VA") is a lipophilic vitamin. The need for vitamin A during animal reproduction and development was first recognized in the early 20th century, including the formation of germ cells, development of embryos, and the like. For example, when lacking vitamin A, the estrus of gilts will be delayed, and even when mating and pregnancy are performed after estrus, mid-trimester miscarriage may happen. It suggests in the prior art that total number of piglets born can be increased by injecting vitamin A into female pigs. A close relationship between vitamin A and animal reproduction is mainly based on that vitamin A can promote the synthesis of estrogen, thereby promoting the development of follicles and the increase of the number of ovulations. Vitamin A begins to repeatedly be applied to the research of animal reproduction regulation. However, there is no published data suggesting that vitamin A may be used for ameliorating or avoiding the decrease of uterine receptivity or pregnancy outcome after exogenous gonadotropin treatment.

Moreover, according to the regulations in "China Pig Nutrition Requirement" and "Pig Nutrition Requirement" by academician Defa Li et al., the vitamin A requirement of lean gilts is 5000 IU/kg, and the vitamin A requirement of fat gilts is 1700 IU/kg. In contrast, the National Research Council (NRC) stipulates that the vitamin A requirement of gilts is 1300 IU/kg. However, the inventors found through experiments that even if a gilt was fed with a daily ration satisfying the above vitamin A requirement, it was still difficult to effectively alleviate the uterine receptivity damage and a poor pregnancy outcome after exogenous gonadotropin treatment. This indicates that there may be other factors affecting reproductive performance of gilts and that the mere provision of vitamin A does not solve these problems. Therefore, further research and exploration of other possible nutritional or environmental factors are needed to improve reproductive performance.

N-Acetylcysteine (also referred to herein as "NAC") has a chemical name of N-acetyl-L-cysteine and a molecular formula of $C_5H_9NO_3S$, and has such functions as improving respiration, resisting oxidation, and enhancing body immunity and the like. The inventors through numerous experimental studies, and found that N-acetylcysteine has effects on inhibiting ERK phosphorylation in endometrium, and vitamin A can inhibit expression of ERα. Significant better results were obtained when NAC and VA were combined than singly. The inventors particularly found that additionally administering an amount of vitamin A can synergistically enhance the effect of NAC, and can effectively inhibit over-activation of ERα-FGF-pERK-cell cycle signaling pathway and inhibit the over-proliferation of endometrial epithelial cells, thereby improving uterine receptivity and a pregnancy outcome after exogenous gonadotropin treatment, such as improving embryo implantation rate, status of embryo development status of embryo development after implantation, pregnancy rate, live birth, and the like. Neither NAC nor VA has toxicity to mammals, and can together improve the reproductive performance of female animals, and has a wide application prospect in fields of assisted reproduction and animal reproduction. However, Neither the previous studies nor the prior art suggests application of N-acetylcysteine in combination with vitamin A to ameliorate or avoid the decrease in uterine receptivity and to improve a poor pregnancy outcome after exogenous gonadotropin treatment.

For this, in one aspect of the disclosure, it is provided a method for ameliorating or avoiding the adverse effect of exogenous gonadotropins on reproductive performance. According to one embodiment of the disclosure, the method comprises: feeding N-acetylcysteine and vitamin A to the female animals prior to the treatment with the exogenous gonadotropins; after the feeding with N-acetylcysteine and vitamin A, the ERα-FGF-PERK-cell cycle signaling pathway of the female animals is inhibited so as to improve uterine receptivity and a pregnancy outcome by the exogenous gonadotropins; the mass ratio of the N-acetylcysteine to the vitamin A is 0.5:1 to 8:1; the dose of the N-acetylcysteine is 60 mg/kg BW/day to 200 mg/kg BW/day, and the dose of the vitamin A is 25 mg/kg BW/day to 120 mg/kg BW/day.

According to the method provided by an embodiment of the disclosure, through the combined use of NAC and VA, the over-activation of ERα-FGF-pERK-cell cycle signaling pathway after exogenous gonadotropin treatment can be effectively inhibited, the effect of exogenous gonadotropins on the reproductive performance of female animals is reduced or eliminated, and the uterine receptivity and pregnancy outcome, such as embryo implantation rate, status of embryo development after implantation, pregnancy rate, live birth, and the like, can be improved. Further, the inventors obtained the effective mass ratio and respective doses of NAC and VA after intensive study, and particularly found that additionally administering an amount of vitamin A can synergistically enhance the effect of NAC and can further improve the effect of exogenous gonadotropins on reproductive performance of female animals. The method of the disclosure has wide application prospect. For example, it can be used in animal husbandry to realize the reproduction regulation and control management of animals such as swine, horses, cattle, and the like and realize batch production. The method has substantial application value.

According to one embodiment of the disclosure, the method for ameliorating or avoiding the effect of exogenous gonadotropins on reproductive performance of female animals may further have the following additional technical features:

According to one embodiment of the disclosure, 10-15 days prior to the treatment with the exogenous gonadotropins, N-acetylcysteine and vitamin A oral administration is started, and the administration is stopped when pregnancy is first confirmed, at the latest; or 5-7 days prior to the treatment with the exogenous gonadotropins, N-acetylcysteine and vitamin A intraperitoneal administration is started, and the administration is stopped when pregnancy is first confirmed, at the latest; or 3-4 days prior to the treatment with the exogenous gonadotropins, N-acetylcysteine and vitamin A vaginal suppository administration is started, and the administration is stopped when pregnancy is first confirmed, at the latest.

According to one embodiment of the disclosure, the female animal is selected from a gilt and/or a sow the exogenous gonadotropins comprise at least one of the following: pregnant mare serum gonadotropin, equine chorionic gonadotropin, follicle-stimulating hormone, gonadotropin-releasing hormone, and human chorionic gonadotropin.

According to one embodiment of the disclosure, the improvement of uterine receptivity of the female animals treated with exogenous gonadotropins comprise at least one of the following: inhibiting ERα-FGF-pERK-cell cycle signaling pathway and inhibiting mitosis cycle of endometrial epithelial cells; the pregnancy outcome of the female animals treated with exogenous gonadotropins comprise at least one of the following: embryo implantation rate, status of embryo development after implantation, pregnancy rate, and live birth.

In another aspect of the disclosure, it is provided a husbandry method for ameliorating or avoiding effect of exogenous gonadotropins on reproductive performance of female animals. According to one embodiment of the disclosure, the method comprises: orally administering to a gilt altrenogest for 17-19 days, wherein 80-110 mg/kg BW of N-acetylcysteine and 80-110 mg/kg BW of vitamin A are separately added to the feed from day 5 to day 7 until a first pregnancy examination is completed, and the mass ratio of the N-acetylcysteine to the vitamin A is 0.5:1-2:1; at 41-43 hours after oral administration of the altrenogest is stopped, injecting pregnant mare serum gonadotropin into induce follicular development synchronization; at 79-81 hours after the treatment with pregnant mare serum gonadotropin, injecting ovulation induction drugs, at 23-25 hours after the treatment, carrying out a first mating, and then after 15-17 hours, carrying out a second mating. According to one embodiment of the disclosure, the method comprises: sequentially carrying out estrus synchronization treatment, exogenous gonadotropin treatment, ovulation induction treatment, and mating treatment on the female animals; feeding N-acetylcysteine and vitamin A to the female animals prior to the treatment with exogenous gonadotropins.

According to one embodiment of the disclosure, the estrus synchronization treatment comprises: feeding a gilt with altrenogest for 14-18 days or synchronously weaning a sow, wherein the feeding amount is 15-25 mg/day; the exogenous gonadotropins treatment comprises: treating with an exogenous gonadotropin to the female animals at day 1.5 to day 2 after the estrus synchronization treatment; the ovulation induction treatment comprises: treating with an ovulation induction drugs after 70 hours to 90 hours by the exogenous gonadotropins treatment; the mating treatment comprises: carrying out a first mating after an interval of 20 hours to 28 hours for the female animals treated by the ovulation induction treatment, and then carrying out a second mating after 14 hours to 16 hours.

In yet another aspect of the disclosure, it is provided a method for improving reproductive performance of a subject treated with exogenous gonadotropins comprising administrating the subject with a combination of N-acetylcysteine and vitamin A; wherein the mass ratio of the N-acetylcysteine to the vitamin A is 0.5:1 to 8:1.

In one embodiment of the disclosure, a uterine receptivity, a pregnancy outcome, and offspring health condition of the subject treated with exogenous gonadotropins is improved by the treatment with N-acetylcysteine and vitamin A to inhibiting ERα-FGF-pERK-cell cycle signaling pathway.

According to one embodiment of the disclosure, wherein the improvement of uterine receptivity of the subject treated with exogenous gonadotropins comprise at least one of the following: inhibiting ERα-FGF-pERK-cell cycle signaling pathway and inhibiting mitosis cycle of endometrial epithelial cells.

According to one embodiment of the disclosure, wherein the pregnancy outcome of the subject treated with exogenous gonadotropins comprise at least one of the following: embryo implantation rate, status of embryo development after implantation, pregnancy rate, and live birth.

According to one embodiment of the disclosure, wherein the exogenous gonadotropins comprise at least one of the following: pregnant mare serum gonadotropin, equine chorionic gonadotropin, follicle-stimulating hormone, gonadotropin-releasing hormone, and human chorionic gonadotropin.

According to one embodiment of the disclosure, wherein the administration route of the N-acetylcysteine in combination with the vitamin A is independently selected from oral administration, intragastric administration, intraperitoneal injection, intravenous injection, intravenous drip, intramuscular injection, or subcutaneous injection.

According to one embodiment of the disclosure, wherein the dosage form of the N-acetylcysteine in combination with the vitamin A is independently selected from oral liquid, injections, tablets, capsules, vaginal suppositories, or films.

According to one embodiment of the disclosure, wherein, wherein the subject is human, the method is for assisted reproduction.

According to one embodiment of the disclosure, the method can effectively ameliorate or avoid the uterine receptivity and pregnancy outcome after exogenous gonadotropins, such as improving embryo implantation rate, status of embryo development after implantation, pregnancy rate, health conditions of born offspring, and the like, and has important significance in assisted reproduction technology.

According to an embodiment of the disclosure, the assisted reproduction uses fresh embryo transfer.

Additional aspects and advantages of the disclosure will in part be illustrated in the following description and become apparent from the following description, or may be learned by practice of the disclosure.

BRIEF DESCRIPTION OF THE DRAWINGS

The aforementioned and/or additional aspects and advantages of the disclosure will become apparent and easily understood from the description of the embodiments with reference to the following drawings, in which:

(FIG. 1A) Immunofluorescence results show that the expression of the estrogen receptor ERα is significantly increased after gonadotropin treatment. (FIG. 1B) The mRNA expression level of the endometrial FGF family gene is increased after gonadotropin treatment. (FIG. 1C) Immunofluorescence and immunohistochemistry results show that the endometrial pFGFR2 and pERK are overexpressed; the endometrial cavity epithelial proliferation marker molecule Ki67 is overexpressed.

(FIG. 3A) VA administered alone or in combination with NAC significantly inhibits exogenous gonadotropin-induced ERα overexpression; (FIG. 3B) and (FIG. 3C) NAC alone or in combination with NAC can significantly inhibit exogenous gonadotropin-induced pERK overexpression; (FIG. 3D) Regulation pattern of NAC and VA on ERα-FGF-PERK-cell cycle signaling pathway.

(FIG. 4A) Administration of NAC in combination with VA in a specific ratio can significantly alleviate exogenous gonadotropin-induced decrease of embryo implantation. (FIG. 4B) Administration of NAC in combination with VA in a specific ratio can significantly alleviate exogenous gonadotropin-induced decrease of live birth. (FIG. 4C) The fetus regressed after BGJ398 treatment.

(FIG. 5A) Grouping of frozen embryo transfer and fresh embryo transfer. The control group is IVF fresh embryos transferred in natural estrus, the frozen group is IVF frozen embryos transferred 3 weeks after the female mice are treated with an exogenous gonadotropin, and the NAC+VA group is IVF fresh embryos transferred after the female mice are treated with an exogenous gonadotropin. (FIG. 5B) and (FIG. 5C) Administration of NAC in combination with VA allows the number of implantation sites and live birth of the mice to reach the level of the control group.

(FIG. 6A) The transcriptome sequencing of the livers of offspring mice born by frozen and fresh embryo transfer shows that the gene expression pattern of the frozen embryo group is partially changed, and the gene expression pattern of the offspring mice of the NAC in combination with VA treatment group is closer to that of the control group. (FIG. 6B) The differential genes which are down-regulated in the frozen embryo group are mainly enriched in the pathways of NADH dehydrogenase activity, oxidative phosphorylation, sugar metabolism, and the like.

DETAILED DESCRIPTION

Figure 1:
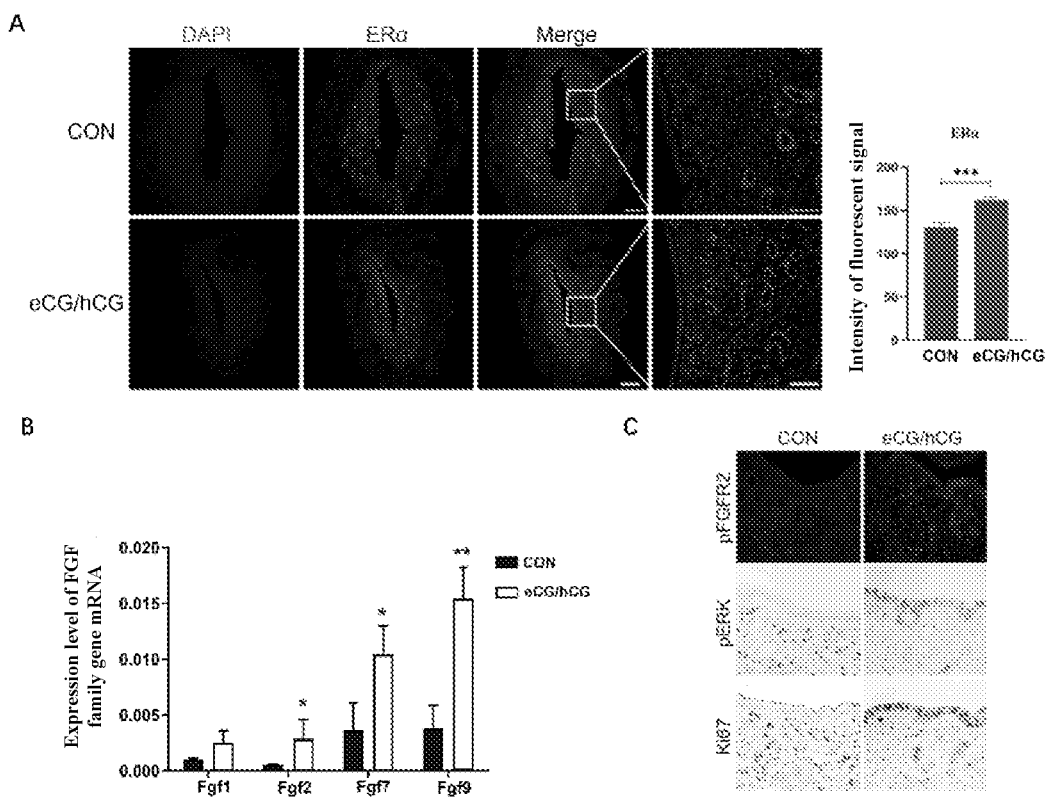
FIGS. 1A-1C shows the molecular mechanism analysis of effect of exogenous gonadotropins on mouse uterine receptivity.
Figure 2:
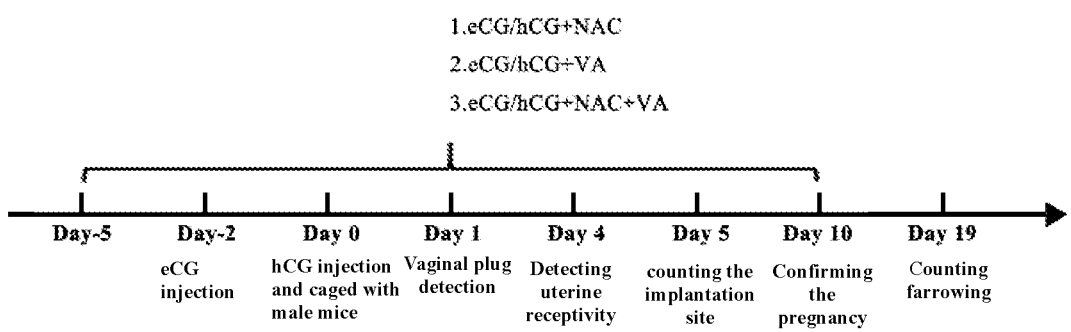
FIG. 2 shows the timing of the administration of NAC and VA alone and in combination.
Figure 3:
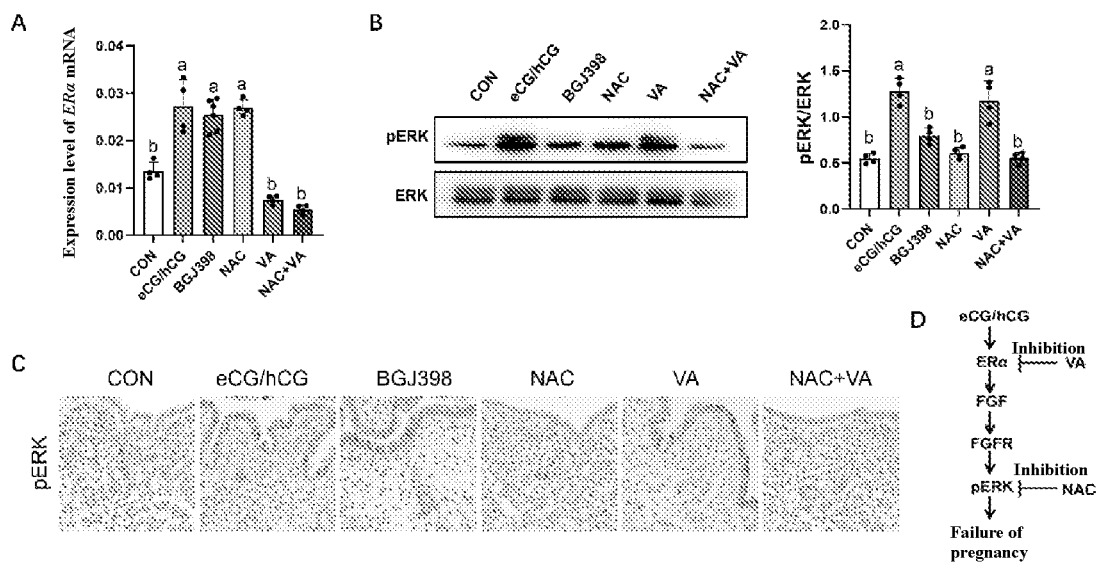
FIGS. 3A-3D shows the molecular mechanism analysis of NAC and VA inhibiting ERα-FGF-pERK-cell cycle signaling pathway and thereby regulating the establishment of uterine receptivity.

Examples of the disclosure are described in detail below. The following examples are exemplary and illustrative only, and should not be construed as limiting the disclosure.

It should be noted that the terms "first" and "second" are used for descriptive purposes only and should not be construed as indicating or implying relative importance or implicitly indicating the number of indicated technical features. Therefore, features defined with "first" and "second" may explicitly or implicitly include one or more of the features. Further, in the description of the disclosure, "a plurality of" means two or more unless otherwise specified.

The endpoints of the ranges and any values disclosed herein are not limited to the precise ranges or values, and these ranges or values should be understood to encompass values close to these ranges or values. For numerical ranges, the endpoint values of each range, the endpoint values of each range and single point values, as well as single point values, can be combined with each other to obtain one or more new numerical ranges, which should be construed as being specifically disclosed herein.

The term "comprise", "comprises" or "comprising" is open-ended, i.e., including what is meant by the disclosure, but not excluding other aspects.

The disclosure provides a method for ameliorating or avoiding the effect of exogenous gonadotropins on reproductive performance of female such as domestic animals, human and the like, each of which is described in detail below.

Husbandry Method

In one aspect of the disclosure, it is provided a husbandry method for ameliorating or avoiding the effect of exogenous gonadotropins on reproductive performance of female animals.

According to one embodiment of the disclosure, N-acetylcysteine and vitamin A are fed to the female animals prior to the treatment of female animals with the exogenous gonadotropin;

after the feeding with N-acetylcysteine and vitamin A, the ERα-FGF-PERK-cell cycle signaling pathway of the female animals is inhibited to improve uterine receptivity and a pregnancy outcome by the exogenous gonadotropin treatment;

the mass ratio of the N-acetylcysteine to the vitamin A is 0.5:1 to 8:1; the dose of the N-acetylcysteine is 60 mg/kg BW/day to 200 mg/kg BW/day, and the dose of the vitamin A is 25 mg/kg BW/day to 120 mg/kg BW/day.

According to the method provided by one embodiment of the disclosure, through the combined use of NAC and VA, the over-activation of ERα-FGF-pERK-cell cycle signaling pathway after exogenous gonadotropin treatment can be effectively inhibited, the effect of exogenous gonadotropins on the reproductive performance of female animals is reduced or eliminated, and the uterine receptivity and pregnancy outcome, such as embryo implantation rate, status of embryo development after implantation, pregnancy rate, live birth, and the like, can be improved.

Further, the inventors obtained the effective mass ratio and respective doses of NAC and VA after intensive studiy, and particularly found that additionally administering an amount of vitamin A nearly a hundred times or more than that in the regular daily ration can synergistically enhance the effect of NAC and can further improve the effect of exogenous gonadotropins on reproductive performance of female animals. This method has a wide application prospect, for example, in animal husbandry to realize the reproduction regulation and control management of animals such as swine, horses, cattle, and the like and realize batch production. The method has substantial application value.

According to one embodiment of the disclosure, the mass ratio of the N-acetylcysteine to the vitamin A is 0.5:1 to 8:1. For example, the mass ratio may be 0.5:1, 0.75:1, 1:1, 1.5:1, 2:1, 2.5:1, 3:1, 3.5:1, 4:1, 4.5:1, 5:1, 8:1, or a range value formed by any two values as the endpoints. Therefore, the ERα-FGF-pERK-cell cycle signaling pathway can be better synergistically inhibited, and the uterine receptivity and pregnancy outcome after exogenous gonadotropin treatment can be improved, such as improving embryo implantation rate, status of embryo development after implantation, pregnancy rate, live birth, and the like.

According to one embodiment of the disclosure, the dose of the N-acetylcysteine is 60 mg/kg BW/day to 200 mg/kg BW/day, and the dose of the vitamin A is 25 mg/kg BW/day to 120 mg/kg BW/day. In some embodiments, the N-acetylcysteine is fed at a dose of 60 mg/kg BW/day, 80 mg/kg BW/day, 100 mg/kg BW/day, 120 mg/kg BW/day, 150 mg/kg BW/day, 180 mg/kg BW/day, 200 mg/kg BW/day, or a range value formed by any two values as the endpoints, and the vitamin A is fed at a dose of 30 mg/kg BW/day, 60 mg/kg BW/day, 100 mg/kg BW/day, 120 mg/kg BW/day, or a range value formed by any two values as the endpoints. "kg BW" refers to the body weight of the female animals in kilograms (kg). Therefore, it is beneficial to better synergistically inhibiting the ERα-FGF-pERK-cell cycle signaling pathway, and improving the uterine receptivity and pregnancy outcome after exogenous gonadotropins treatment, such as improving embryo implantation rate, status of embryo development after implantation, pregnancy rate, live birth, and the like. Particularly, additionally administering an amount of vitamin A can synergistically enhance the effect of NAC and can further improve the effect of an exogenous gonadotropins on reproductive performance of female animals.

According to one embodiment of the disclosure, 10-15 days prior to the treatment with the exogenous gonadotropin, N-acetylcysteine and vitamin A oral administration is started, and the administration is stopped when pregnancy is first confirmed, at the latest; or 5-7 days prior to the treatment with the exogenous gonadotropin, N-acetylcysteine and vitamin A intraperitoneal administration is started, and the administration is stopped when pregnancy is first confirmed, at the latest; or 3-4 days prior to the treatment with the exogenous gonadotropin, N-acetylcysteine and vitamin A vaginal suppository administration is started, and the administration is stopped when pregnancy is first confirmed, at the latest. Specifically, pregnancy can be confirmed by conventional means such as B-mode ultrasound and pregnancy reaction. It can be understood that the administration of NAC and VA may be stopped when pregnancy is first confirmed, at any time during pregnancy, or when pregnancy is completed, wherein stopping the administration when pregnancy is first confirmed can both improve uterine receptivity and a pregnancy outcome after exogenous gonadotropin treatment, and can reduce the workload and cost of manipulation associated with the additional administration of NAC and VA.

Herein, the term "female animals" refers to a female animal domesticated by human and whose reproduction can be artificially controlled, such as swine, cattle, sheep, horses, donkeys, camels, rabbits, etc. According to one embodiment of the disclosure, the female animals is selected from a gilt and/or a sow.

According to one embodiment of the disclosure, the improvement of uterine receptivity of the female animals treated with the exogenous gonadotropins comprises at least one of the following: inhibiting ERα-FGF-pERK-cell cycle signaling pathway and inhibiting mitosis cycle of endometrial epithelial cells; the pregnancy outcome of the female animals treated with the exogenous gonadotropin comprises at least one of the following: embryo implantation rate, status of embryo development after implantation, pregnancy rate, and live birth.

According to one embodiment of the disclosure, the exogenous gonadotropin comprises at least one of the following: pregnant mare serum gonadotropin, equine chorionic gonadotropin, follicle-stimulating hormone, gonadotropin-releasing hormone, and human chorionic gonadotropin.

According to one embodiment of the disclosure, the method comprises: sequentially carrying out estrus synchronization treatment, exogenous gonadotropin treatment, ovulation induction treatment, and mating treatment on the female animals; feeding N-acetylcysteine and vitamin A to the female animals prior to the treatment of female animals with the exogenous gonadotropin. Therefore, it is beneficial to realizing batch production and improving the batch production efficiency.

According to one embodiment of the disclosure, the estrus synchronization treatment comprises: feeding a gilt with altrenogest for 14-18 days or synchronously weaning a sow; the exogenous gonadotropin treatment comprises: on day 1.5 to day 2 after the estrus synchronization treatment, injecting an exogenous gonadotropin into the female animals; the ovulation induction treatment comprises: at 70 hours to 90 hours for the female animals treated by the exogenous gonadotropin, injecting an ovulation induction drug; the mating treatment comprises: carrying out a first mating after 20 hours to 28 hours for the female animals treated by the ovulation induction treatment, and then carrying out a second mating after 14 hours to 16 hours.

In addition, the disclosure provides another husbandry method for ameliorating or avoiding the effect of exogenous gonadotropins on reproductive performance of female animals, the method comprises: orally administering to a gilt altrenogest for 17-19 days, wherein 80-110 mg/kg BW of N-acetylcysteine and 80-110 mg/kg BW of vitamin A are separately added to the feed from day 5 to day 7 until a first pregnancy examination is completed, and the mass ratio of the N-acetylcysteine to the vitamin A is 0.5:1-2:1;

at 41-43 hours after oral administration of the altrenogest is stopped, injecting pregnant mare serum gonadotropin to induce follicular development synchronization;

at 79-81 hours after treated with the pregnant mare serum gonadotropin, injecting an ovulation induction drugs, at 23-25 hours after the injection, carrying out a first mating, and then after 15-17 hours, carrying out a second mating. Therefore, the method of the disclosure can effectively improve the reproductive performance of female animals treated by an exogenous gonadotropin, including the uterine receptivity and pregnancy outcome, such as embryo implantation rate, status of embryo development after implantation, pregnancy rate, live birth, and the like. Moreover, N-acetylcysteine and vitamin A have synergistic effect and have wide application prospect. For example, they can be used in animal husbandry to realize the reproduction regulation and control management of animals including domestic animals such as swine, horses, cattle, and the like and realize batch production. The method has substantial application value.

Assisted Reproduction Method

In yet another aspect of the disclosure, it is provided a method for improving reproductive performance of a subject treated with exogenous gonadotropins comprising administrating the subject with a combination of N-acetylcysteine and vitamin A, the mass ratio of the N-acetylcysteine to the vitamin A is 0.5:1 to 8:1. the combination of N-acetylcysteine and vitamin A is administrated for improving reproductive performance of a subject treated with exogenous gonadotropins and for inhibiting ERα-FGF-pERK-cell cycle signaling pathway to improve uterine receptivity, a pregnancy outcome, and offspring health condition of the subject treated with the exogenous gonadotropin.

Herein, the term "subject" refers to any invertebrate or vertebrate subject, including but not limited to: humans and other primates, including non-human primates, such as chimpanzees and other apes and monkeys; animals including domestic animals such as cattle, sheep, pigs, goats, and horses; domestic mammals, such as dogs and cats; laboratory animals, including rodents, such as mice, rats, and guinea pigs; birds, including domestic, wild and game birds such as chickens, turkeys, and other chickens, ducks, geese, and the like; insects, nematodes, fish, amphibians, reptiles, and the like, in particular viviparous therian mammals, including humans, rats, pigs, cattle, sheep, horses, cats, dogs, and the like. When the subject is a human, NAC and VA can be used in the preparation of assisted reproduction drugs for improving uterine receptivity and/or a pregnancy outcome and/or health condition of born offspring during assisted reproduction.

According to one embodiment of the disclosure, the improvement of uterine receptivity after the treatment with the gonadotropin comprises at least one of the following: inhibiting ERα-FGF-pERK-cell cycle signaling pathway and inhibiting mitosis cycle of endometrial epithelial cells; the pregnancy outcome after the treatment with the gonadotropin comprises at least one of the following: embryo implantation rate, status of embryo development after implantation, pregnancy rate, and the number of offspring.

According to one embodiment of the disclosure, the exogenous gonadotropin comprises at least one of the following: pregnant mare serum gonadotropin (also referred to in the disclosure as "PMSG"), equine chorionic gonadotropin (also referred to in the disclosure as "eCG"), follicle-stimulating hormone (also referred to in the disclosure as "FSH"), gonadotropin-releasing hormone (also referred to in the disclosure as "GnRH"), and human chorionic gonadotropin (also referred to in the disclosure as "hCG").

According to one embodiment of the disclosure, the administration route of the N-acetylcysteine in combination with the vitamin A is independently selected from oral administration, intragastric administration, intraperitoneal injection, intravenous injection, intravenous drip, intramuscular injection, or subcutaneous injection.

According to one embodiment of the disclosure, the dosage form of the N-acetylcysteine in combination with the vitamin A is independently selected from oral liquid, injections, tablets, capsules, vaginal suppositories, or films.

According to one embodiment of the disclosure, the N-acetylcysteine in combination with the vitamin A is used for assisted reproduction and for inhibiting ERα-FGF-PERK-cell cycle signaling pathway to improve uterine receptivity, a pregnancy outcome, and offspring health condition of the subject treated with the exogenous gonadotropins; the mass ratio of the N-acetylcysteine to the vitamin A is 0.5:1 to 8:1. Therefore, the combination of N-acetylcysteine in combination with the vitamin A can effectively improve the uterine receptivity and pregnancy outcome after exogenous gonadotropins, such as improving embryo implantation rate, status of embryo development after implantation, pregnancy rate, offspring health, and the like, and has important significance in the field of assisted reproduction.

According to one embodiment of the disclosure, the assisted reproduction is selected from fresh embryo transfer. Through the combined administration of NAC and VA, the number of offspring born by fresh embryo transfer can be improved, and the offspring health problem caused by embryo cryopreservation can be eliminated.

According to one embodiment of the disclosure, the improvement of uterine receptivity after the treatment with the gonadotropin comprises at least one of the following: inhibiting ERα-FGF-pERK-cell cycle signaling pathway and inhibiting mitosis cycle of endometrial epithelial cells; the pregnancy outcome after the treatment with the gonadotropin comprises at least one of the following: embryo implantation rate, status of embryo development after implantation, pregnancy rate, and live birth.

According to one embodiment of the disclosure, the administration route of the N-acetylcysteine in combination with the vitamin A is independently selected from oral administration, intragastric administration, intraperitoneal injection, intravenous injection, intravenous drip, intramuscular injection, or subcutaneous injection.

According to one embodiment of the disclosure, the dosage form of the N-acetylcysteine in combination with the vitamin A is independently selected from oral liquid, injections, tablets, capsules, vaginal suppositories, or films.

According to one embodiment of the disclosure, it is provided a method for assisting reproduction, improving reproductive performance of female mammals, alleviating gonadotropin-induced uterine receptivity decrease and/or a poor pregnancy outcome, and improving pregnancy uterine receptivity and/or pregnancy outcome in assisted reproduction, wherein the method comprises: administering to a subject the N-acetylcysteine and vitamin A described above.

The term "treat", "treating" or "treatment" is used herein to mean obtaining a desired pharmacological and/or physiological effect. The effect may be prophylactic in terms of completely or partially preventing a disease or a symptom thereof, and/or may be therapeutic in terms of partially or completely curing a disease and/or an adverse effect arising from the disease. As used herein, "treat", "treating" or "treatment" encompasses a disease in mammals, particularly humans, including: (a) preventing the occurrence of a disease or disorder in an individual susceptible to the disease but not yet diagnosed; (b) inhibiting a disease, e.g., arresting disease progression; or (c) alleviating a disease, e.g., alleviating a symptom associated with the disease. As used herein, "treat", "treating" or "treatment" encompasses any administration of a drug to an individual to treat, cure, alleviate, ameliorate, reduce or inhibit a disease in the individual, including but not limited to administration of a drug comprising the combined drug described herein to an individual in need.

The scheme of the disclosure will be explained with reference to the following examples. Those skilled in the art will appreciate that the following examples are only for illustrating the disclosure, and should not be construed as limitations to the scope of the disclosure. The examples without a specified particular technique or condition are performed in accordance with techniques or conditions described in literatures in the art or in accordance with the product specification. Reagents or instruments without specified manufacturers used herein are conventional products that are commercially available.

Example 1

Method for Improving Embryo Implantation and Live Birth after Gonadotrophin Treatment by Using N-Acetylcysteine in Combination with Vitamin A 1. Experimental Animals All experimental mice in the experiment were purchased from SPF (Beijing) Biotechnology Co., Ltd. The female mice were 8 weeks old, and the male mice were 10 weeks old. After the experimental mice were purchased, all the mice were provided with free access to water and food under a light control environment (12 h of light:12 h of darkness) without special experimental requirements. The feeding environment was controlled at 20-24° C.

2. Experimental Design 2.1 Molecular Signaling Pathway Change Affecting Uterine Receptivity Decrease after Mouse Ovulation Stimulation In the animal experiment, ICR female mice (SPF grade, 8 weeks old, 28-30 g) were selected and randomized into groups of 10-18, including normal control group (CON) and superovulation stimulation group (eCG/hCG). The temperature of the breeding environment was 22° C., 12-h light/dark cycle was performed, and the mice were provided with free access to water and food. After the animals were purchased, they were acclimated for 5-7 days.

Control group (CON): A female 8-week-old ICR mouse was taken as the research object, subjected to natural estrus, and mated with a vasoligated male mouse. After a vaginal plug was observed, the mouse was taken as the control group. The uterus of the mouse was then separated on day 4 after the vaginal plug was observed, namely, when the uterine receptivity was established, and the detection of a plurality of signal molecules was carried out.

Superovulation stimulation group (eCG/hCG): A female 8-week-old ICR mouse was taken as the research object, injected with 10 IU eCG at 6 pm, injected with 10 IU hCG after an interval of 48 h to induce superovulation, and was then in the same cage with a vasoligated male mouse. The next morning, the vaginal plug was checked. After a vaginal plug was observed, the mouse was taken as the superovulation stimulation group. The uterus of the mouse was then separated on day 4 after the vaginal plug was observed, namely, when the uterine receptivity was established, and the detection of a plurality of signal molecules was carried out.

Endometrial samples of the mice in the CON group and the eCG/hCG group on day 4 of pregnancy were separately collected for molecular detection. The detection indexes include ERα, FGF family gene, FGF receptor, pERK, and epithelial cell proliferation signal molecule Ki67 staining. The molecular indexes of influence of an exogenous gonadotropin on uterine receptivity decrease were explored.

2.2 Molecular Regulation Effect of N-Acetylcysteine in Combination with Vitamin A on Alleviating Uterine Receptivity Decrease Induced by Gonadotropin Treatments 1) Grouping of Experimental Animals In the animal experiment, ICR female mice (SPF grade, 8 weeks old, 28-30 g) were selected and randomized into groups of 10-18, including normal control group (CON), superovulation stimulation group (eCG/hCG), superovulation stimulation and BGJ398 group (eCG/hCG+BGJ398), superovulation stimulation and NAC single administration group (eCG/hCG+NAC), superovulation stimulation and VA single administration group (eCG/hCG+VA), superovulation stimulation and NAC and VA combined administration group (eCG/hCG+NAC+VA). The temperature of the breeding environment was 22° C., 12-h light/dark cycle was performed, and the mice were provided with free access to water and food. After the animals were purchased, they were acclimated for 5-7 days.

Control group (CON): A female 8-week-old ICR mouse was taken as the research object, subjected to natural estrus, mated with a vasoligated male mouse, and was taken as the control group. The uterus of the mouse was then separated on day 4 after the vaginal plug was observed, namely, when the uterine receptivity was established, and the detection of a plurality of signal molecules was carried out.

Superovulation stimulation group (eCG/hCG): A female 8-week-old ICR mouse was taken as the research object, injected with 10 IU eCG at 6 pm, injected with 10 IU hCG after 48 h to induce superovulation, and was then in the same cage with a vasoligated male mouse. The next morning, the vaginal plug was checked. After a vaginal plug was observed, the mouse was taken as the superovulation stimulation group. The uterus of the mouse was then separated on day 4 after the vaginal plug was observed, namely, when the uterine receptivity was established, and the detection of a plurality of signal molecules was carried out.

Superovulation stimulation and BGJ398 group (eCG/hCG+BGJ398): Female 8-week-old ICR mice were taken as the research object and injected with 10 IU eCG and PMSG to induce superovulation, respectively. On day 3 after the vaginal plug was observed, the mice were injected with 5 μL of FGF receptor inhibitor containing 100 μM BGJ398 inhibitor through the uterine horn. The uterus of the mouse was then separated on day 4 after the vaginal plug was observed, namely, when the uterine receptivity was established, and the detection of a plurality of signal molecules was carried out.

Superovulation stimulation and NAC single administration group (eCG/hCG+NAC): A female 8-week-old ICR mouse was taken as the research object. On the basis of the treatment of the superovulation stimulation group (eCG/hCG), each mouse was intraperitoneally injected with NAC at a dose of 200 mg/kg BW daily 5 days prior to the injection of eCG. The uterus of the mouse was then separated on day 4 after the vaginal plug was observed, namely, when the uterine receptivity was established, and the detection of a plurality of signal molecules was carried out.

Superovulation stimulation and VA single administration group (eCG/hCG+VA): A female 8-week-old ICR mouse was taken as the research object. On the basis of the treatment of the superovulation stimulation group (eCG/hCG), each mouse was intraperitoneally injected with VA at a dose of 200 mg/kg BW daily 5 days prior to the injection of eCG/hCG. The uterus of the mouse was then separated on day 4 after the vaginal plug was observed, namely, when the uterine receptivity was established, and the detection of a plurality of signal molecules was carried out.

Superovulation stimulation and NAC and VA combined administration group (eCG/hCG+NAC+VA): A female 8-week-old ICR mouse was taken as the research object. On the basis of the treatment of the superovulation stimulation group (eCG/hCG), each mouse was intraperitoneally injected with a mixture of NAC at a dose of 100 mg/kg BW and VA at a dose of 100 mg/kg BW daily 5 days prior to the injection of eCG. The uterus of the mouse was then separated on day 4 after the vaginal plug was observed, namely, when the uterine receptivity was established, and the detection of a plurality of signal molecules was carried out.

The timing of the single and combined administrations is shown in the schematic diagram 2.

2) Molecular Index Detection

Endometrial samples of the mice in the CON group, eCG/hCG group, eCG/hCG+BGJ398 group, eCG/hCG+NAC group, eCG/hCG+VA group, and eCG/hCG+NAC+VA group on day 4 of pregnancy were separately collected for molecular detection. The detection indexes include key molecules such as ERα, pERK, and the like which participate in the induction of uterine receptivity decrease by an exogenous gonadotropin.

2.3 Method for Alleviating Mouse Reproductive Performance after Gonadotropin Treatment by Using N-Acetylcysteine in Combination with Vitamin A 1) Grouping of Experimental Animals In the animal experiment, ICR female mice (SPF grade, 8 weeks old, 28-30 g) were selected and randomized into groups of 10-18, including normal control group (CON), superovulation stimulation group (eCG/hCG), superovulation stimulation and BGJ398 group (eCG/hCG+BGJ398), superovulation stimulation and NAC single administration group (eCG/hCG+NAC), superovulation stimulation and VA single administration group (eCG/hCG+VA), superovulation stimulation and NAC and VA combined administration group (eCG/hCG+NAC+VA). The temperature of the breeding environment was 22° C., 12-h light/dark cycle was performed, and the mice were provided with free access to water and food. After the animals were purchased, they were acclimated for 5-7 days.

Control group (CON): A female 8-week-old ICR mouse was taken as the research object, subjected to natural estrus, mated with a vasoligated male mouse, and was taken as the control group recipient mice. Embryo transfer was then performed on day 4 after the vaginal plug was observed.

Superovulation stimulation group (eCG/hCG): A female 8-week-old ICR mouse was taken as the research object, injected with 10 IU eCG at 6 pm, injected with 10 IU hCG after an interval of 48 h to induce superovulation, and was then in the same cage with a vasoligated male mouse. The next morning, the vaginal plug was checked. After a vaginal plug was observed, the mouse was taken as the superovulation stimulation group recipient. Embryo transfer was then performed on day 4 after the vaginal plug was observed.

Superovulation stimulation and BGJ398 group (eCG/hCG+BGJ398): Female 8-week-old ICR mice were taken as the research object and injected with 10 IU eCG and PMSG to induce superovulation, respectively. On day 3 of pregnancy, the mice were injected with 5 μL of FGF receptor inhibitor containing 100 μM BGJ398 inhibitor through the uterine horn. Embryo transfer was then performed on day 4 after the vaginal plug was observed.

Superovulation stimulation and NAC single administration group (eCG/hCG+NAC): A female 8-week-old ICR mouse was taken as the research object. On the basis of the treatment of the superovulation stimulation group (eCG/hCG), each mouse was intraperitoneally injected with NAC at a dose of 200 mg/kg BW daily 5 days prior to the injection of eCG. Embryo transfer was then performed on day 4 after the vaginal plug was observed. The injection was continued until day 10 of pregnancy.

Superovulation stimulation and VA single administration group (eCG/hCG+VA): A female 8-week-old ICR mouse was taken as the research object. On the basis of the treatment of the superovulation stimulation group (eCG/hCG), each mouse was intraperitoneally injected with VA at a dose of 200 mg/kg BW daily 5 days prior to the injection of eCG/hCG. Embryo transfer was then performed on day 4 after the vaginal plug was observed. The injection was continued until day 10 of pregnancy.

Superovulation stimulation and NAC and VA combined administration group (eCG/hCG+NAC+VA): A female 8-week-old ICR mouse was taken as the research object. On the basis of the treatment of the superovulation stimulation group (eCG/hCG), each mouse was intraperitoneally injected with a mixture of NAC at a dose of 100 mg/kg BW and VA at a dose of 100 mg/kg BW daily 5 days prior to the injection of eCG. Embryo transfer was then performed on day 4 after the vaginal plug was observed. The injection was continued until day 10 of pregnancy.

The timing of the single and combined administrations is shown in the schematic diagram 2.

2) Embryo Transfer Experiment

The mice in the CON group, eCG/hCG group, eCG/hCG+BGJ398 group, eCG/hCG+NAC group, eCG/hCG+VA group, and eCG/hCG+NAC+VA group were separately in the same cage and mated with a vasoligated male mouse. The vaginal plug was checked at about 8 am in the next morning. The pseudopregnant female mouse whose vaginal plug was observed was ready for transfer. The day when the vaginal plug was observed was taken as day 1, and day 4 was the date of blastocyst transfer. Each mouse had 6 IVF blastocysts transferred to each side of uterine horn, and then was placed in the animal house for normal feeding.

3) Statistics of Embryo Implantation

Embryo transfer was separately performed on the mice in the CON group, eCG/hCG group, eCG/hCG+BGJ398 group, eCG/hCG+NAC group, eCG/hCG+VA group, and eCG/hCG+NAC+VA group on day 4 of pregnancy; embryo implantation sites were counted by orbital injection of Chicago blue on day 5 of pregnancy.

4) Statistics of Live Birth

Embryo transfer was separately performed on the mice in the CON group, eCG/hCG group, eCG/hCG+BGJ398 group, eCG/hCG+NAC group, eCG/hCG+VA group, and eCG/hCG+NAC+VA group on day 4 of pregnancy, and the mice were then placed in the animal house for normal feeding. On the day of delivery, the number born alive index was counted.

3. Experimental Results

Molecular detection experiments show that the eCG/hCG ovulation promotion treatment causes excessive activation of the endometrial "ERα-FGF-PERK-cell cycle" signaling pathway (FIGS. 1A-1C), further causes uterine receptivity abnormality, and finally causes embryo implantation failure. Therefore, the disclosure takes the "inhibition of the overactivation of ERα-FGF-pERK-cell cycle signaling pathway" as a new target for alleviating the side effect of eCG/hCG on endometrium. In the disclosure, the FGF receptor inhibitor BGJ398 and the NAC (N-acetylcysteine) and VA (vitamin A) selected by previous drug screening were used as candidate drugs. Further signal molecule detection shows that VA can significantly inhibit the expression of ERα, BGJ398 and NAC can significantly inhibit excessive phosphorylation of pERK, and NAC in combination with VA has synergistic effect on inhibiting ERα-FGF-pERK signaling pathway (FIGS. 3A-3D).

2.4 Method for Alleviating Mouse Reproductive Performance after Gonadotropin Treatment by N-Acetylcysteine in Combination with Vitamin A.

1) Grouping of Experimental Animals

In the animal experiment, ICR female mice (SPF grade, 8 weeks old, 28-30 g) were selected and randomized into groups of 10-18. The exogenous gonadotropin treatment group was taken as the control group (CON). The BGJ398 group (BGJ398), NAC single administration group (NAC), VA single administration group (VA), VC single administration group (VC), melatonin (MT) single administration group (MT), NAC and VA combined administration group (NAC+VA) in different ratios, NAC and Vc combined administration group (NAC+Vc), and VA and MT combined administration group (VA+MT) were administered under the condition of exogenous gonadotropin treatment. The temperature of the breeding environment was 22° C., 12-h light/dark cycle was performed, and the mice were provided with free access to water and food. After the animals were purchased, they were acclimated for 5-7 days.

The specific treatment was as follows:

A female 8-week-old ICR mouse was taken as the research object, injected with 10 IU eCG at 6 pm, injected with 10 IU hCG after an interval of 48 h to induce superovulation, and was then in the same cage with a vasoligated male mouse. The next morning, the vaginal plug was checked. After a vaginal plug was observed, the mouse was taken as the recipient after exogenous gonadotropin treatment. Embryo transfer was then performed on day 4 after the vaginal plug was observed. The administration dose and time in the other groups are shown in Table 1. The timing of the single and combined administrations is shown in the schematic diagram 2.

TABLE 1

Administration dose and time in different groups

| Group | Exogenous gonadotropin treatment | Administration dose of drug | Administration time of drug | Time of embryo transfer and number of embryo transferred |
|---|---|---|---|---|
| CON | Injected with 10 IU eCG at 6 pm, and injected with 10 IU hCG after an interval of 48 h | — | — | Day 4 after mating with vasoligated male mouse; 12 embryos/recipient mice |
| BGJ398 | Same as above | 100 μM | Day 3 after mating with vasoligated male mouse | Same as above |
| NAC | Same as above | 200 mg/Kg BW | From 5 days prior to eCG injection to day 10 of pregnancy | Same as above |
| VA (vitamin A) | Same as above | 200 mg/Kg BW | Same as above | Same as above |
| VC (vitamin C) | Same as above | 200 mg/Kg BW | Same as above | Same as above |
| MT (melatonin) | Same as above | 200 mg/Kg BW | Same as above | Same as above |
| NAC + VA(1:1) | Same as above | NAC: 100 mg/Kg BW VA: 100 mg/Kg BW | Same as above | Same as above |
| NAC + VA(0.1:1) | Same as above | NAC: 20 mg/Kg BW VA: 180 mg/Kg BW | Same as above | Same as above |
| NAC + VA(9:1) | Same as above | NAC: 180 mg/Kg BW VA: 20 mg/Kg BW | Same as above | Same as above |
| NAC + VC(1:1) | Same as above | NAC: 100 mg/Kg BW VC: 100 mg/Kg BW | Same as above | Same as above |
| VA + MT(1:1) | Same as above | NAC: 100 mg/Kg BW MT: 100 mg/Kg BW | Same as above | Same as above |

2) Statistics of Embryo Implantation and Live Birth

The mice in each group described above (5-9 mice/group) were counted for the embryo implantation sites by orbital injection of Chicago blue on the second day of embryo transfer. The remaining groups of mice (5-9 mice/group) were placed in the animal house for normal feeding. On the day of delivery, the number born alive index was counted.

Figure 4:
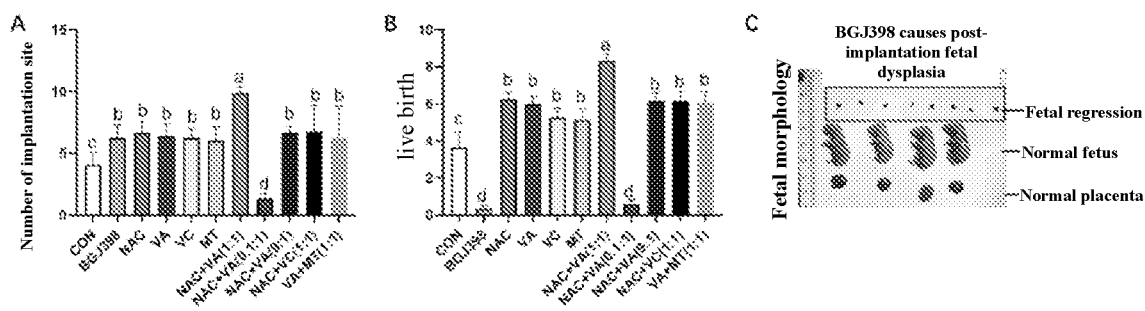
FIGS. 4A-4C shows the analysis of the alleviation of exogenous gonadotropin-induced decreases of embryo implantation and live birth by NAC and VA.

3) Experimental Results it further detected use of N-acetylcysteine in combination with vitamin A in alleviating mouse reproductive performance after gonadotropin treatment. As a result, the number of implantation sites of BGJ398 group (injected with FGF receptor inhibitor BGJ398 through uterine horn) mice on day 5 after pregnancy was found to be significantly higher than that of the control group (FIG. 4A); however, after tracking the pregnancy live birth data, BGJ398, as a small molecule inhibitor, was found to be highly toxic to fetal development, causing developmental regression of the fetus after implantation (FIG. 4B and FIG. 4C). VC is VA analogue. MT is melatonin, and also has effects of resisting oxidation and promoting reproduction. However, they do not work well either alone or in synergy with NAC/VA.

When mice were separately injected with NAC at a dose of 200 mg/kg BW or VA at a dose of 200 mg/kg BW alone, the number of implantation sites and live births can be increased to some extent (FIG. 4A and FIG. 4B). When NAC and VA were administered in combination at a ratio of 1:1, the mice had significantly higher implantation sites and live births than those of the control group, and significantly higher than either NAC or VA group administered alone; when NAC and VA were administered in combination at a ratio of 0.1:1, the mice had significantly lower implantation sites and live births than those of the control group; when NAC and VA were administered in combination at a ratio of 9:1, the mice had no significant difference in implantation sites and live births from either NAC or VA single administration group. This further indicates that NAC and VA (0.5:1 to 8:1) in a proper ratio have a synergistic effect on ameliorating or avoiding side effects of an exogenous gonadotropin and improving a pregnancy outcome.

Example 2

Method for Improving Health Condition of Offspring after Frozen Embryo Transfer by Using N-Acetylcysteine in Combination with Vitamin A 1. Experimental Design In the field of assisted reproduction, because an exogenous gonadotropin causes uterine receptivity decrease, the fresh embryo is not suitable for direct use of transfer. The fresh embryo is usually frozen and stored first, and then transferred after the side effects caused by the exogenous gonadotropin are relieved, but the frozen storage of the embryo has certain influence on the health condition of the embryo and newborn. For this reason, on the basis of improving the reproductive performance of mice treated by an gonadotropin using N-acetylcysteine in combination with vitamin A, the disclosure introduces the fresh embryo, which is beneficial to the health condition of the newborn.

2. Experimental Animals and Grouping

Figure 5:
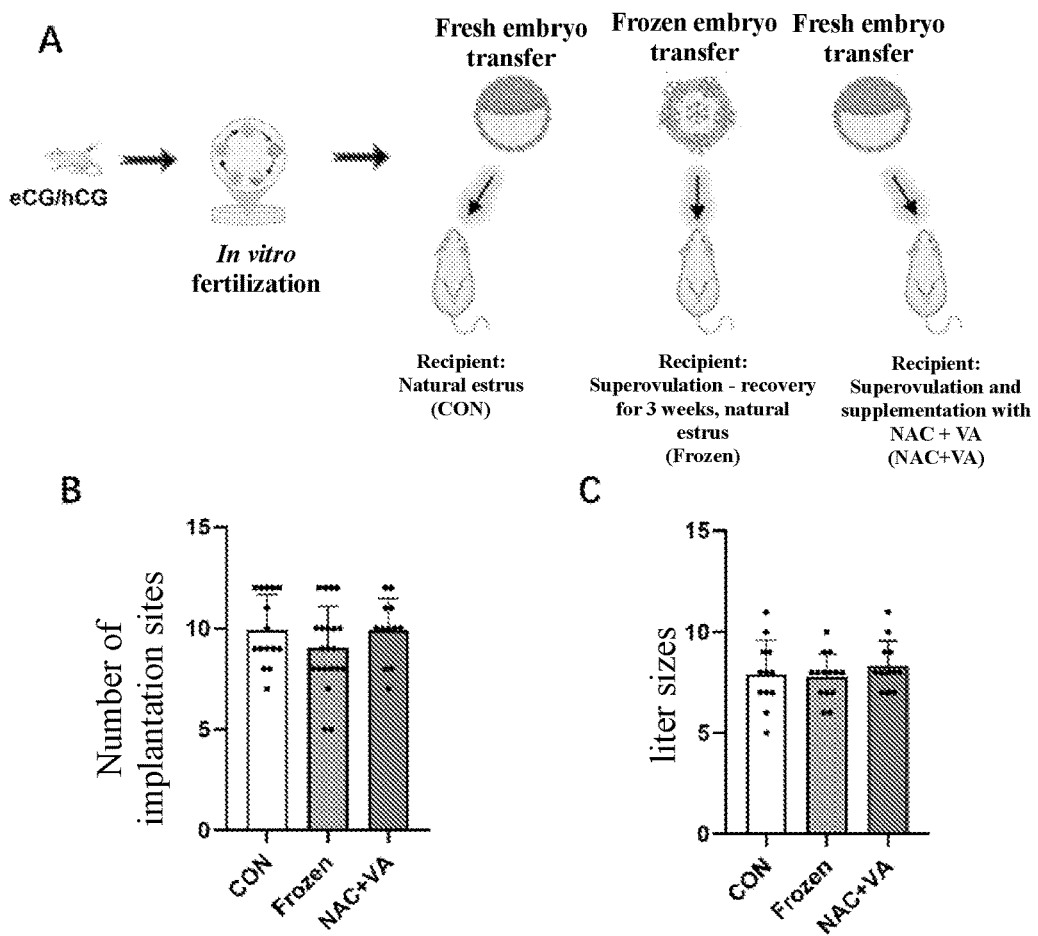
FIGS. 5A-5C shows the analysis of the effect of combined administration of NAC and VA on fresh embryo transfer.

In the animal experiment, ICR female mice (SPF grade, 8 weeks old, 28-30 g) were selected and randomized into groups of 10-18, including IVF fresh embryo transferred into natural estrus cycle recipient group (CON group), IVF frozen embryo transferred into interval cycle recipient group (Frozen group), and IVF fresh embryo transferred into ovarian stimulated and supplemented with NAC in combination with VA recipient group (NAC+VA group) (FIG. 5A). The temperature of the breeding environment was 22° C., 12-h light/dark cycle was performed, and the mice were provided with free access to water and food. After the animals were purchased, they were acclimated for 5-7 days.

CON group: A female 8-week-old ICR mouse was taken as the research object, subjected to natural estrus, mated with a vasoligated male mouse, and was taken as the control group recipient mice. IVF fresh embryo transfer was then performed on day 4 after the vaginal plug was observed.

Frozen group: A female 8-week-old ICR mouse was taken as the research object, injected with 10 IU eCG at 6 pm, injected with 10 IU hCG after an interval of 48 h to induce superovulation, then placed for 3 weeks, subjected to natural estrus again, mated with a vasoligated male mouse, and taken as the Frozen group recipient mouse. IVF Frozen embryo transfer was then performed on day 4 after the vaginal plug was observed.

NAC+VA group: A female 8-week-old ICR mouse was taken as the research object. On the basis of the treatment of the superovulation stimulation group (eCG/hCG), each mouse was intraperitoneally injected with a mixture of NAC at a dose of 100 mg/kg BW and VA at a dose of 100 mg/kg BW daily 5 days prior to the injection of eCG. IVF fresh embryo transfer was then performed on day 4 after the vaginal plug was observed. The NAC+VA mixture was continuously injected until day 10 of pregnancy.

3. Statistics of Embryo Implantation and Live Birth

Embryo transfer was separately performed on the mice in the CON group, Frozen group, and NAC+VA group on day 4 of pregnancy; embryo implantation sites were counted by orbital injection of Chicago blue on day 5 of pregnancy.

Embryo transfer was separately performed on the mice in the CON group, Frozen group and NAC+VA group on day 4 of pregnancy, and the mice were then placed in the animal house for normal feeding. On the day of delivery, the number born alive index was counted.

4. Transcriptome Analysis of Liver Tissue of Newborn Mice

Embryo transfer was separately performed on the mice in the CON group, Frozen group and NAC+VA group on day 4 of pregnancy, and the mice were then placed in the animal house for normal feeding. On the day of delivery, liver tissues of the newborn mice were isolated and used for transcriptome sequencing, followed by GO and KEGG analyses on the transcriptome data.

5. Analysis of Results

Figure 6:
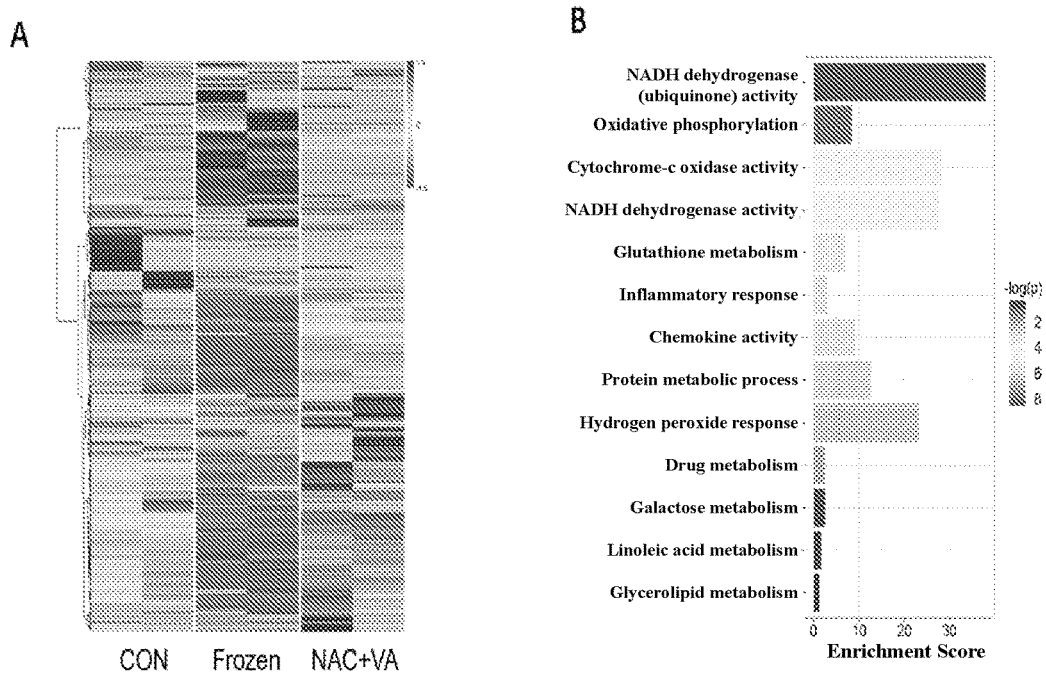
FIGS. 6A and 6B shows the analysis of the effect of combined administration of NAC and VA on health conditions of offspring born individuals.

The results show that there was no significant difference in embryo implantation number and live birth in the three groups CON, Frozen, and NAC+VA (FIG. 5B and FIG. 5C), which demonstrated that NAC in combination with VA can effectively alleviate the exogenous gonadotropin-induced uterine receptivity decrease with reference to example 1. Further transcriptome sequencing of the livers of offspring mice born by frozen and fresh embryo transfer shows that the gene expression pattern of the frozen embryo group was partially changed, and the gene expression pattern of the offspring mice of the NAC in combination with VA treatment group was closer to that of the control group (FIG. 6A). Moreover, the differential genes which were down-regulated in the frozen embryo group were mainly enriched in the pathways of NADH dehydrogenase activity, oxidative phosphorylation, sugar metabolism, and the like (FIG. 6B), which indicates that the liver metabolism of the mice born by the frozen embryo transfer was abnormal. The combined administration of NAC and VA in a proper ratio (0.5:1 to 8:1) can improve the number of offspring born by fresh embryo transfer without affecting the health condition of the offspring born.

Example 3

Method for Batch Farrowing (Fixed-Time Artificial Insemination) by Using N-Acetylcysteine in Combination with Vitamin A 1. Experimental Animals All the experimental female pigs were provided by Henan Xinda Husbandry Co., Ltd. Gilts with the weight of 120-140 kg and the age of 200-250 days were selected for the experiment.

2. Sow Batch Experimental Design 2.1 Influence of N-Acetylcysteine in Combination with Vitamin A on Embryonic Development in Batch Farrowing with FTAI 1) Grouping of Experimental Animals and Treatment Procedure Gilts with the weight of 120-140 kg and the age of 200-250 days were selected for the experiment, which were divided into five groups of the CON group, eCG/GnRH group, eCG/GnRH+NAC group, eCG/GnRH+VA group, and eCG/GnRH+NAC+VA group for the experiment. Each group had 6-8 gilts.

The technical process of batch farrowing of the gilts in the eCG/GnRH group (namely the batch farrowing with FTAI scheme) was as follows: 1) estrus synchronization treatment: the gilt orally taken altrenogest for 18 days; 2) after an interval of 42 h after the estrus synchronization treatment, exogenous gonadotropin eCG was injected to induce follicular development synchronization; 3) after an interval of 80 h after eCG injection, an ovulatio induction drugs (GnRH) was injected. After an interval of 24 h after the injection, a first mating was carried out, and then after an interval of 16 h, a second mating was carried out.

On the basis of the technical process of batch farrowing of the gilts in the eCG/GnRH group, in the eCG/GnRH+NAC group, eCG/GnRH+VA group, and eCG/GnRH+NAC+VA group, NAC at a dose of 200 mg/kg BW, VA at a dose of 200 mg/kg BW, and combined addition of NAC (100 mg/kg BW) and VA (100 mg/kg BW) were separately added into the feed daily 14 days prior to the eCG injection until the end of first pregnancy examination (day 30-32 of pregnancy).

The technical process of batch farrowing of the gilts in the CON group (namely the simple batch farrowing scheme) was as follows: 1) estrus synchronization treatment: the gilt orally taken altrenogest for 18 days; 2) the gilt was subjected to natural estrus, and the estrus of the gilt was confirmed by artificial heat detection; 3) a first mating was carried out after the gilt stood estrus, and then after an interval of 16 h, a second mating was carried out.

2) Detection of Fetal Development and Farrowing after Embryo Implantation

On day 19 of pregnancy, 6-8 gilts in each group were slaughtered, and embryos were recovered by washing the uterine horn of the pregnant gilt. The development of embryos of different treatment groups was compared.

3) Experimental Results

Figure 7:
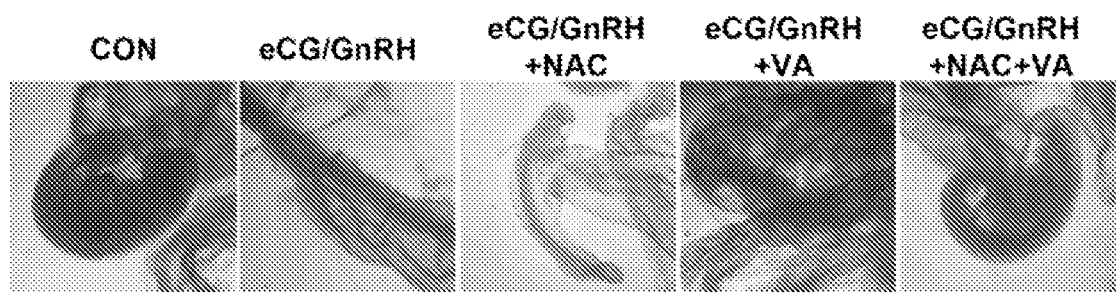
FIG. 7 shows the analysis of the effect of combined administration of NAC and VA on fetal development in batch farrowing with FTAI. The combined administration of NAC and VA is effective in alleviating hindered fetal development caused by exogenous gonadotropin treatment.

The results are shown in FIG. 7. Compared with the simple batch farrowing, the batch farrowing with FTAI resulted in delayed embryo development due to exogenous gonadotropin treatment, and the combined administration of NAC and VA significantly improved the development state of embryos, which was closer to that of embryos without exogenous gonadotropin treatment (control group).

2.2 Influence of N-Acetylcysteine in Combination with Vitamin A on Reproductive Performance of Female Pigs in Batch Farrowing with FTAI 1) Grouping of Experimental Animals and Treatment Procedure Gilts with the weight of 120-140 kg and the age of 200-250 days were selected for the experiment, which were divided into the batch farrowing with FTAI (CON) group, batch farrowing supplemented with NAC (NAC) group, batch farrowing supplemented with VA (VA) group, batch farrowing with combined administration of NAC and VA (NAC+VA 1:1) group, batch farrowing with combined administration of NAC and VA (NAC+VA 0.1:1) group, and batch farrowing with combined administration of NAC and VA (NAC+VA 9:1) group. Each group had 48-55 gilts.

The technical process of batch farrowing of the gilts in the CON group (namely the batch farrowing with FTAI scheme) was as follows: 1) estrus synchronization treatment: the gilt orally taken altrenogest for 18 days; 2) after an interval of 42 h after the estrus synchronization treatment, exogenous gonadotropin eCG was injected to induce follicular development synchronization; 3) after an interval of 80 h after eCG injection, an ovulatio induction drugs (GnRH) was injected. After an interval of 24 h after the injection, a first mating was carried out, and then after an interval of 16 h, a second mating was carried out. Pregnancy examination was then performed and the gilts were fed normally until delivery.

On the basis of the technical process of batch farrowing of the gilts in the CON group, in the NAC group, VA group, and NAC+VA group, NAC at a dose of 200 mg/kg BW, VA at a dose of 200 mg/kg BW, combined addition of NAC (100 mg/kg BW) and VA (100 mg/kg BW), combined addition of NAC (20 mg/kg BW) and VA (180 mg/kg BW), and combined addition of NAC (180 mg/kg BW) and VA (20 mg/kg BW) were separately added into the feed daily 14 days prior to the eCG injection until the end of first pregnancy examination (day 30-32 of pregnancy). The gilts were then fed normally until delivery.

2) Statistics of Farrowing

The pregnancy rate of the female pigs was counted through pregnancy examination; the farrowing rate of the female pigs was counted during delivery. The pregnancy rate and the farrowing rate of female pigs from different treatment groups were calculated as follows: Female pig pregnancy rate=pregnant female pig count/mated female pig count×100% Female pig farrowing rate=delivery female pig count/mated female pig count×100%

3) Experimental Results

As can be seen from Table 2, compared with the female pig pregnancy rate and farrowing rate of the batch farrowing with FTAI, supplementation of NAC or VA alone can significantly improve the female pig pregnancy rate and farrowing rate; when NAC and VA were administered in combination at a ratio of 1:1, the female pig pregnancy rate and farrowing rate were significantly higher than those of the group supplemented with NAC or VA alone; however, when NAC and VA were administered in combination at a ratio of 0.1:1, the female pig pregnancy rate and farrowing rate were lower than that of the control group; when NAC and VA were administered in combination at a ratio of 9:1, the female pig pregnancy rate and farrowing rate were not significantly different from the group supplemented with NAC or VA alone. Therefore, NAC and VA in a proper ratio have synergistic effect (Table 2).

TABLE 2

Influence of NAC in combination with VA on female pig pregnancy rate and farrowing rate in precise batch farrowing

| Group | Number of experimental animals | Estrus detection rate (%) | Number of mated animals | Pregnancy Rate (%) | Farrowing rate (%) |
|---|---|---|---|---|---|
| CON group | 55 | 92.73 | 55 | 77.42$^a$ | 70.97$^a$ |
| NAC group | 54 | 88.89 | 54 | 85.19$^b$ | 81.48$^b$ |
| VA Group | 48 | 93.75 | 48 | 89.58$^b$ | 83.33$^b$ |
| NAC + VA (1:1) group | 50 | 92.00 | 50 | 96.00$^c$ | 92.00$^c$ |
| NAC + VA (0.1:1) group | 53 | 92.45 | 53 | 71.70$^d$ | 60.38$^d$ |
| NAC + VA (9:1) group | 52 | 92.31 | 52 | 86.54$^b$ | 82.69$^b$ |

Note:
Different lowercase letters indicate significant differences, $P < 0.05$.

Advantages of the Disclosure

Aiming at the problems of low pregnancy rate, low farrowing rate, and the like caused by exogenous gonadotropins, the disclosure, with the combined use of NAC and VA, establishes a method for alleviating decreases of uterine receptivity and a poor pregnancy outcome induced by exogenous gonadotropins. Compared with the prior art, the method significantly improves the pregnancy rate and farrowing rate after exogenous gonadotropin treatment on the premise of causing side effects by exogenous gonadotropin treatment, and has great value for large-scale promotion of batch farrowing and improvement of assisted reproduction in China.

Although the disclosure has been described in detail with respect to the general description and the specific embodiments thereof, it will be apparent to those skilled in the art that modifications or improvements can be made based on the disclosure. Accordingly, these modifications or improvements made without departing from the spirit of the disclosure fall within the scope of protection of the disclosure.

Although the embodiments of the present disclosure have been shown and described above, it can be understood that the foregoing embodiments are exemplary and should not be understood as limitations on the disclosure. A person of ordinary skill in the art can make changes, modifications, replacements, and variations to the foregoing embodiments within the scope of the disclosure.

The invention claimed is:

1. A husbandry method for ameliorating or avoiding the effect of exogenous gonadotropins on reproductive performance of female animals comprising:
   feeding a composition having active ingredients consisting of only N-acetylcysteine and vitamin A to the female animals prior to the treatment with the exogenous gonadotropins;
   after feeding the composition, an ERα-FGF-pERK-cell cycle signaling pathway of the female animals is inhibited to improve uterine receptivity and a pregnancy outcome by the exogenous gonadotropin treatment; and
   the mass ratio of the N-acetylcysteine to the vitamin A is 0.5:1 to 2:1, and the dose of the vitamin A is 60 mg/kg BW/day to 120 mg/kg BW/day,
   wherein the female animal is selected from a gilt or a sow.

2. The method according to claim 1, wherein
   10-15 days prior to the treatment with the exogenous gonadotropins, oral administration of the composition is started, and the administration is stopped when pregnancy is first confirmed, at the latest; or
   5-7 days prior to the treatment with the exogenous gonadotropins, intraperitoneal administration of the composition is started, and the administration is stopped when pregnancy is first confirmed, at the latest; or
   3-4 days prior to the treatment with the exogenous gonadotropins, vaginal suppository administration of the composition is started, and the administration is stopped when pregnancy is first confirmed, at the latest.

3. The method according to claim 1, wherein
   the exogenous gonadotropins are selected from the group consisting of: pregnant mare serum gonadotropin, equine chorionic gonadotropin, follicle-stimulating hormone, gonadotropin-releasing hormone, and human chorionic gonadotropin, or mixtures thereof;
   the improvement of uterine receptivity of the female animals treated with the exogenous gonadotropins is inhibiting the ERα-FGF-PERK-cell cycle signaling pathway and/or inhibiting a mitosis cycle of endometrial epithelial cells; and
   the pregnancy outcome of the female animals treated with the exogenous gonadotropins is selected from the group consisting of: an embryo implantation rate, a status of embryo development after implantation, a pregnancy rate and a live birth, or combinations thereof.

4. The method according to claim 1, wherein the method comprises:
   sequentially carrying out estrus synchronization treatment, exogenous gonadotropin treatment, ovulation induction treatment, and mating treatment on the female animals; and
   feeding the composition to the female animals prior to the treatment with the exogenous gonadotropins.

5. The method according to claim 4, wherein
   the estrus synchronization treatment comprises: feeding a gilt with altrenogest for 14-18 days or synchronously weaning a sow;
   the exogenous gonadotropins treatment comprises: treating with an exogenous gonadotropin to the female animals at day 1.5 to day 2 after the estrus synchronization treatment;
   the ovulation induction treatment comprises: treating with ovulation induction drugs after 70 hours to 90 hours by the exogenous gonadotropins treatment; and
   the mating treatment comprises: carrying out a first mating after 20 hours to 28 hours for the female animals treated by the ovulation induction treatment, and then carrying out a second mating after 14 hours to 16 hours.

6. A husbandry method for ameliorating or avoiding the adverse effect of exogenous gonadotropins on reproductive performance of female animals comprising:
   orally administering to a gilt altrenogest for 17-19 days, wherein only 80-110 mg/kg BW of N-acetylcysteine and 80-110 mg/kg BW of vitamin A are separately added to the feed from day 5 to day 7 until a first pregnancy examination is completed, and the mass ratio of the N-acetylcysteine to the vitamin A is 0.5:1-2:1;
   at 41-43 hours after oral administration of the altrenogest is stopped, injecting pregnant mare serum gonadotropin to induce follicular development synchronization;
   at 79-81 hours after the injection of pregnant mare serum gonadotropin, injecting ovulation induction drugs; and
   at 23-25 hours after the injection of ovulation induction drugs, carrying out a first mating, and then after 15-17 hours, carrying out a second mating.

* * * * *